United States Patent [19]

Widmer et al.

[11] 4,140,843
[45] Feb. 20, 1979

[54] NUCLEAR HALOGENATED α,α'-BIS(CYCLOPENTADIENYL)XYLENE

[75] Inventors: Franz Widmer, Basel; Alfred Renner, Muenchenstein; Heinz Rembold, Arlesheim, all of Switzerland

[73] Assignee: Ciba-Geigy AG, Basel, Switzerland

[21] Appl. No.: 839,087

[22] Filed: Oct. 3, 1977

Related U.S. Application Data

[63] Continuation of Ser. No. 483,593, Jun. 27, 1974, abandoned, which is a continuation of Ser. No. 289,186, Sep. 14, 1972, abandoned, which is a continuation-in-part of Ser. No. 48,456, Jun. 22, 1970, abandoned, which is a continuation-in-part of Ser. No. 696,724, Jan. 10, 1965, abandoned.

[30] Foreign Application Priority Data

Jan. 16, 1967 [CH] Switzerland ............... 567/67

[51] Int. Cl.$^2$ ............ C08F 132/08; C08F 32/08; C08G 61/12; C08C 61/00
[52] U.S. Cl. ........................ 528/392; 526/283; 526/308; 260/648 C; 260/648 F; 260/649 R; 260/649 F
[58] Field of Search ............ 526/11.1, 308, 283

[56] References Cited

U.S. PATENT DOCUMENTS 2,726,232  12/1965  Upson ................. 526/308

FOREIGN PATENT DOCUMENTS 6800177  1/1960  South Africa.

Primary Examiner—Herbert J. Lilling
Attorney, Agent, or Firm—Vincent J. Cavalieri

[57] ABSTRACT

New halogenated bis(cyclopentadienyl) compounds of the general formula

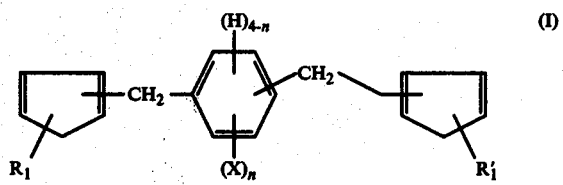

in which X represents a halogen atom having an atomic number of at most 35, that is to say a fluorine, bromine or preferably chlorine atom, $R_1$ and $R_1'$ each represents a hydrogen atom or a methyl group, and n = 1, 2, 3 or 4.

The monomer of the formula (I) undergoes spontaneous dimerization or oligomerization respectively after it is formed. The oligomer has the formula

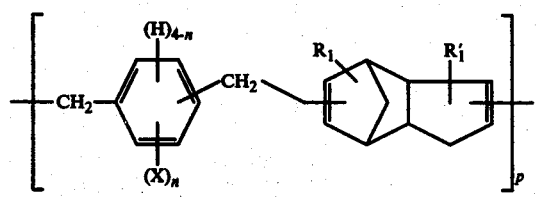

where p is 2 to 20.

7 Claims, No Drawings

NUCLEAR HALOGENATED α,α'-BIS(CYCLOPENTADIENYL)XYLENE

This is a continuation of application Ser. No. 483,593 filed on June 27, 1974, now abandoned, which is a continuation of Ser. No. 289,186, filed on Sept. 14, 1972, now abandoned, which is a continuation-in-part-application of our copending application Ser. No. 48,456, filed June 22, 1970, which in turn is continuation-in-part-application of our application Ser. No. 696,724, filed Jan. 10, 1965, both now abandoned.

It is known that monomeric or oligomeric bis(cyclopentadienyl)alkanes, -aralkanes and -silanes can be manufactured by reacting dihalogene-alkanes, -aralkanes or -silanes respectively with alkali metal or Grignard compounds of cyclopentadiene or of its methyl homologues. Compared with the monomeric bis(cyclopentadienyl) compounds the oligomeric bis(cyclopentadienyl) compounds have the industrially important advantages of greater ease of manufacture, stability under industrial storage and transport conditions and better processing properties, for example in casting, moulding or laminating processes. The manufacture and use of such bis(cyclopentadienyl) compounds have been described, for example, in U.S. Pat. No. 2,726,232, in French Specifications Nos. 1,345,817, 1,345,818 and 1,350,732 and in the publication by A. Renner and collaborators "Ueber neue, durch polydienaddition härtbare Kunststoffe" in "Kunststoffe," vol. 53, No. 8, pages 509 – 513 [1963].

Applicants' own unpublished experiments in which alkali metal compounds of cyclopentadiene were reacted in stoichiometric proportions with compounds whose molecule contains more than 2 chlorine atoms, such as 1,2,3-trichloropropane, tetra(chloromethyl)methane, cyanuric chloride or silicon tetrachloride, in many cases furnished even during the synthesis crosslinked products which on account of their insolubility and infusibility could no longer be shaped. Such results were, after all, certainly to be expected because the polymerization or oligomerization of compounds containing 3 or more cyclopentadienyl residues gives rise from the start to branched or crosslinked macromolecules. On the other hand, when it was attempted to react only two halogen atoms of the above-mentioned compounds containing 3 or more halogen atoms by using less than a stoichiometric proportion of the alkali metal compound of cyclopentadiene, this reaction yielded in most cases dark-coloured, badly defined, resinous substances which decomposed at the high temperatures required for their curing and formed black, blistered shaped bodies of no industrial value whatsoever.

The present invention is based on the unexpected observation that dimeric or oligomeric α,α'-bis(cyclopentadienyl)tetrachloro-xylenes are obtained in good yield when bis(chloromethyl)tetrachlorobenzenes are reacted with cyclopentadienyl sodium.

In view of the above-mentioned negative results of the reaction of cyclopentadienyl sodium with other organic compounds containing 3 or more chlorine atoms, this smooth progress of the reaction was unexpected also because it was known that highly halogenated aromatic compounds, for example hexachlorobenzene or pentachlorotoluene require no drastic conditions for the reaction with nucleophilic reagents.

The dimeric or oligomeric α,α'-bis(cyclopentadienyl) tetrachloro-xylenes are new compounds which, apart from the self-extinguishing properties of shaped articles made therefrom, offer a number of unexpected industrial advantages over the halogen-free oligomeric α,α'-bis(cyclopentadienyl)xylenes known from literature, namely:

(1) They cure much more rapidly so that they may also be used as resin component for moulding compositions;

(2) they are much less sensitive towards oxidation on protracted exposure to heat.

Notwithstanding the high degree of halogenation the cured oligomers have a little polar character and display very low dielectric constants and low dielectric losses over a wide frequency range. They may therefore be used as electrical insulating materials having outstanding properties, especially in the high-frequency alternating field.

Accordingly, the present invention provides new dimers and oligomers of halogented bis(cyclopentadienyl) compounds of the general formula

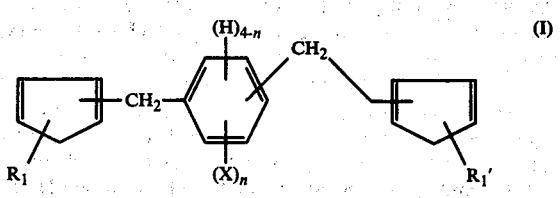

in which X represents a halogen atom of atomic number not greater than 35, that is to say a fluorine, bromine or preferably chlorine atom, $R_1$ and $R_1'$ each represents a hydrogen atom or a methyl group, and n =0 1, 2, 3 or 4.

The dimers and oligomers may have a linear or cyclic structure consisting of the structural elements of the formula

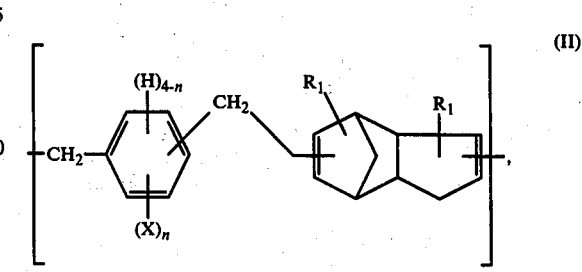

Dimeric compounds of cyclic structure probably have the formula

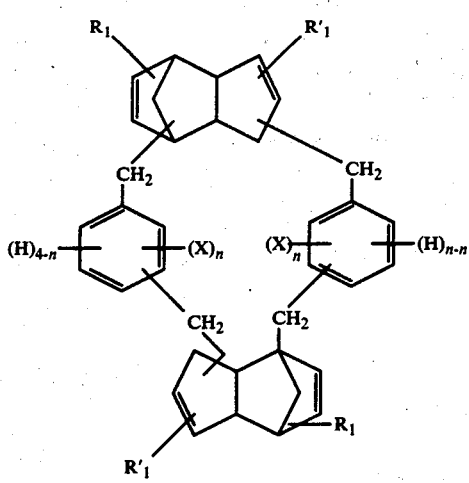

while oligomers having chain structure probably correspond to the formula

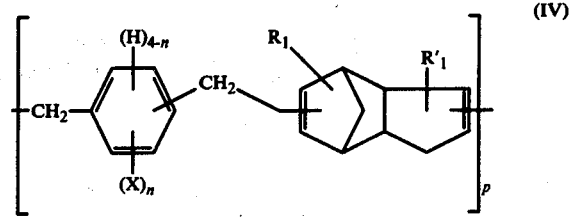

in which the chain ends may be saturated by one of the mechanisms usual in polymerizations, for example a radical or ionic initiating reaction, and chain breaking reaction, either by a combination, disproportionation or chain-transfer mechanism, or by addition of an ion. To ensure particularly good yields the saturation of the chain ends of the oligomers is preferably performed by the small quantity (for example 0.1 to 20 mol%, referred to the quantity of bis(cyclopentadienyl) compound) of a conjugated monodiene present during the oligomerization, especially of a monocyclopentadienyl compound such as cyclopentadiene, α-(cyclopentadienyl)-toluene or α-(cyclopentadienyl)-2,3,4,5,6-pentachlorotoluene.

As a rule, the degree of polymerization P is 2 to 20. Since in many cases there are present mixtures of oligomers having different polymerization degrees P, the experimentally determined magnitude of P is in such a case a mean value so that is need not be a whole number.

Particularly valuable technical properties are found in the oligomers of α, α'-bis(cyclopentadientyl)-2,3,5,6-tetrachloroparaxylene of the probable formula

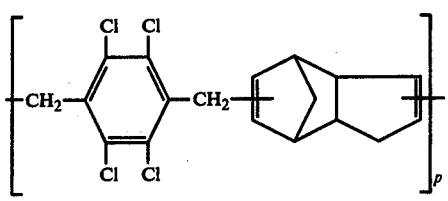

in which P is a number from 2 to 20.

Also very suitable are the oligomers of α,α'-bis (methyl-cyclopentadienyl)-2,3,5,6-tetrachloroparaxylene, α,α'-bis(cyclopentadienyl)-2,3,5,6-tetrafluoroparaxylene, α,α'-bis(cyclopentadienyl)-2,5-difluoro-paraxylene, αα'-bis(cyclopentadienyl)-2,3,5-trichloroparaxylene, α,α'-bis(cyclopentadienyl(-2,4,5,6-tetrachloro-metaxylene, α,α'-bis(cyclopentadienyl)-3,4,5,6-tetrachloro-orthoxylene and α,α'-bis(cyclopentadienyl)-2-bromo-paraxylene.

The new dimerized or oligomerized halogenated bis (cyclopentadienyl) compounds (I) may be prepared according to this invention by reacting a halogen compound of the general formula

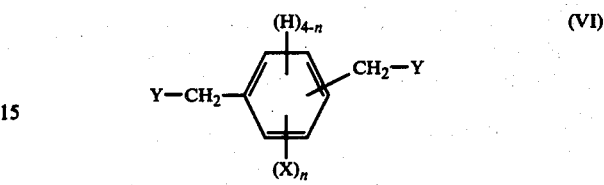

in which X and n have the same meanings as in formula (I) and Y represents a chlorine or bromine atom, with an alkali metal or a Grignard compound of cyclopentadiene or of methylcyclopentadiene with heating, whereby alkali metal halide or magnesium halide respectively is split off and the monomer of the formula (I) is formed which then undergoes spontaneous dimerization or oligomerizaton respectively.

As halogen compounds of the formula (VI) there may be mentioned α,α',3,4,5,6-hexachloro-orthoxylene, α,α',2,4,5,6-hexachloro-metaxylene; α,α'-dichloro-2,3,5,6-tetrafluoro-paraxylene, α,α'-2-tribromo-paraxylene and especially α,α', 2,3,5,6-hexachloro-paraxylene.

Alkali metal compounds of cyclopentadiene suitable for the reaction with the halogen compound (VI) are, for example, cyclopentadiene potassium and especially cyclopentadiene sodium. As a rule there is used a solution of the alkali compound obtained by reacting cyclopentadiene with the alkali metal or sodium in an organic medium, for example toluene and the halogen compound (VI) is added to this solution. The condensation of the halogen compound (VI) with the alkali metal compound of cyclopentadiene is as a rule carried out within the temperature range from 60 to 120° C. During this reaction the initially formed monomer of the formula (I) undergoes autopolymerization to form the dimer or oligomer.

The new dimeric and oligomeric halogenated bis(cyclopentadienyl) compounds are relatively stable at room temperature.

By heating to elevated temperatures the new dimers and oligomers can be cured as such to form insoluble and infusible synthetics suitable for a large variety of industrial uses. A suitable curing temperature is in general within the range from about 130 to 280° C., preferably from 170 to 250° C.; the curing time depends considerably on the curing temperature used.

For some industrial applications it is advantageous to cure in the presence of a curing catalyst, for example a small quantity of a peroxide, whereby curing times of a few minutes at 200° C. become possible. For this purpose there may be used peroxides such as di-tertiary butylperoxide, di-tertiary butylperoxybutane, dilaurylperoxide, dicumylperoxide and tertiary butylcumylperoxide in a concentration of 0.01 to 5%, preferably 0.25 to 0.5%, referred to the weight of the oligomer. Other known curing accelerators, such as cobalt naphthenate, are equally suitable.

The term "curing" as used in this context signifies the conversion of the said dimers and oligomers into crosslinked, insoluble and infusible products.

The crosslinked, infusible products are generally manufactured with simultaneous shaping to furnish shaped articles such as castings, foamed articles, mouldings, lacquer films, laminates, adhesive bonus or the like. For this purpose the dimer alone or in combination with the additives or modifiers conventionally used in the technology of the curable synthetics, such as fillers, plasticizers, solvents, pigments, dyestuffs, mould release agents, flame-proofing agents or the like, are poured into casting moulds, or brushed on to form coatings, or introduced into glued joints or the like and then allowed to cure with heating.

Accordingly, the present invention includes also thermocurable moulding compositions used for the manufacture of shaped articles, including two-dimensional structures, which are characterized by a content of dimerized or oligomerized halogenated bis(cyclopentadienyl) compounds of the formula (I) and, if desired, also of a curing accelerator, especially a peroxide.

The thermocurable moulding compositions of this invention may be used in the unfilled or filled state, if desired in the form of solutions or emulsions, as textile finishes, laminating resins, moulding compositions, sinter powders, injection moulding compositions, paints, lacquers, dipping and casting resins, grouting and sealing compositions, adhesives or the like and for the manufacture of such agents.

The new halogenated oligomers of this invention are particularly suitable for the manufacture of flameproof mouldings and laminates. For the manfacture of moulding compositions there may be admixed with the powdered, solid oligomer conventional fillers, for example glass fibres, mica, quartz meal, cellulose, kaolin, colloidal silica having a large specific surface (AEROSIL ®) or metal powders, and usual mould release agents, for example calcium stearate. For the manufacture of laminates there may, as a rule, first be made the so-called "prepregs" by impregnating two-dimensional materials such as fabrics, fibre mats or fibre fleeces, especially glass fibre mats or glass fibre fabrics, with solutions of the oligomers of this invention in suitable organic solvents, such as benzene, toluene, xylene, solvent naphtha or chlorinated hydrocarbons, such as dichloro-1,2-ethane, trichloroethylene, perchloroethylene, dichloroethyl ether, chlorobenzene or ortho-dichlorobenzene, whereupon the solvent is removed by drying. To improve the adhesion between support and glass fibres it is advantageous first to treat the latter with a suitable adhesion promoter, such as a silane containing vinyl or methacryl groups. The impregnating liquor contains with advantage a small quantity of a curing accelerator, such as a peroxide.

After having removed the solvent it is advantageous to gell in an open press at 130 to 280° C., and then to pre-cure the material in the press under a contact pressure of about 1 to 200 kiloponds/cm². The pre-cured laminate, which already has considerable mechanical stability, can then be further cured without the press under a lighter load, as a rule under a pressure of only up to 0.5 kilopond/cm², at approximately the same temperature in an oven. While also in this case the curing may be finalized in the press, the present process offers the considerable advantage that after a relatively short use of the press, in general for only 1½ to 3½ hours, the substantially less expensive oven curing can be employed.

Apart from good adhesion to glass fibres the oligomers of this invention display also in general adequate adhesion to copper. The adhesion to copper surfaces can be improved by adding to the curable mixture an oligomeric ω,ω'-bis(cyclopentadienyl)alkane, for example 1,6-bis(cyclopentadienyl)hexane. In the manufacture of copper-faced panels with the aid of oligomers of this invention it is thus possible to achieve satisfactory adhesion by compressing a copper foil in a single operation with the corresponding prepreg bundle without using an interlayer. This property, combined with the excellent electrical properties, makes the oligomers of this invention and their mixtures with ω,ω'-bis(cyclopentadienyl)alkanes particularly suitable for the manufacture of copper-faced laminates as base materials for printed circuits.

Parts and percentages in the following Examples are by weight. The relationship between parts by weight and parts by volume is the same as that between the kilogram and the liter.

I. MANUFACTURING EXAMPLES

EXAMPLE 1

Oligomeric α,α'-bis(cyclopentadienyl)2,3,5,6-tetrachloro-paraxylene

23 Parts of sodium metal are fused in 200 parts of toluene, finely dispersed and cooled. 3 Parts of tertiary butanol are added and while providing external cooling 72.6 parts of monomeric cyclopentadiene are stirred in dropwise at 40 to 45° C., and the whole is then kept for 4 hours at 20° C. under nitrogen. In the course of 2 hours at 90° C. a solution, heated at 60° C., of 149 parts of α,α',2,3,5,6-hexachloro-paraxylene in 500 parts of toluene is added and the batch is stirred for another hour at 90° C. Titration of the chlorine ions reveals that a quantitative conversion of the α-positioned chlorine atoms has taken place.

The batch is cooled to room temperature, the sodium chloride formed is filtered off and the filter cake is washed with 3 × 350 parts of toluene. The filtrate is concentrated under reduced pressure, finally for 3 hours at 60° C. under 0.01 mm Hg pressure, to yield 124 parts of a light-yellow solid resin having a softening point of 135° C. (Kofler heater).

| Analysis | calculated | found |
|---|---|---|
| % C | 58.10 | 57.96 |
| % H | 3.79 | 3.84 |
| % Cl | 38.11 | 38.18 |
| Molecular weight: | 950 | |

The molecular weight of 950 is a mean value corresponding to a mixture of dimers and trimers. When more energetic drying conditions (higher temperature and/or longer drying time) are employed, higher molecular weights are obtained which may correspond to tetramers or higher polymers.

To manufacture α,α',2,3,5,6-hexachloro-paraxylene used above 500 parts of 2,3,5,6-tetrachloro-paraxylene are dissolved in 4800 parts of tetrachloromethane. Chlorine is injected under reflux and irradiation with ultraviolet light until the theoretical quantity of HCl has been evolved. The batch is cooled, and the precipitated crystals are filtered off. They melt at 177 to 178° C.

To confirm the formation of the oligomer, the light-yellow solid resin sample (softening point 135° C., mean molecular weight 950) was subject to mass spectrum analysis under the following conditions:
(a) Energy of electrons: 70 e V
(b) Stream of electrons: 300 μ Amp.
(c) Temperature of the sample: 140° C.

Result of the test:
(a) The highest signal m/e 370 (this means the molecular weight of the monomer, containing $^{35}$Cl).
(b) No signals, according to oligomers (n=2, n=3 etc.)
(c) Some signals, according to byproducts:amongst other signals primary signal m/e 335 monomer which lacks 1 Cl-atom
signal m/e 305 monomer which lacks 1 cyclopenatine-group
signal m/e 269 monomer which lacks 1 Cl-atom and 1 cyclopentadine-group
signal m/e 66 cyclopentadiene

EXAMPLE 2

α,α'-Bis(cyclopentadienyl)-2,4,5,6-tetrachloro-metaxylene and its oligomer.

The procedure is the same as in Example 1 except that the 149 parts of α,α'-2,3,5,6-hexachloro-paraxylene are replaced by 149 parts of α,α',2,4,5,6-hexachlorometaxylene [m.p. 139° C.]; α,α'-bis(cyclopentadienyl)-2,4,5,6-tetrachloro-m-xylene is formed, which undergoes spontaneous oligomerization to yield 138 parts of a light-yellow, solid resin having a softening point of 115° C.

| Analysis | calculated | found |
|---|---|---|
| % C | 58.10 | 56.58 |
| % H | 3.79 | 3.83 |
| % Cl | 38.11 | 38.50 |
| Molecular weight: | 1150 | . |

The α,α',2,4,5,6-hexachloro-metaxylene used in this example is prepared as described in Example 1, except that 2,4,5,6-tetrachloro-metaxylene is used instead of 2,3,5,6-tetrachloro-paraxylene.

EXAMPLE 3

Dimeric α,α'-bis(cyclopentadienyl)-3,4,5,6-tetrachloro-orthoxylene

The procedure is as described in Example 1, except that instead of 149 parts of α,α'-2,3,5,6-hexachloroparaxylene 149 parts of α,α'3,4,5,6-hexachloro-orthoxylene [m.p. 76 to 78° C.] are used, to yield 160 parts of a brown, solid resin having a softening point of 60° C.

| Analysis | calculated | found |
|---|---|---|
| % C | 58.10 | 56.68 |
| % H | 3.79 | 3.64 |
| % Cl | 38.11 | 39.9 |
| Molecular weight: | 744 | 623 |

The α,α',3,4,5,6-hexachloro-orthoxylene used in this example is prepared as described in Example 1, except that 3,4,5,6-tetrachloro-orthoxylene instead of 2,3,5,6-tetrachloro-paraxylene is used.

EXAMPLE 4

Oligomeric α,α'-bis(cyclopentadienyl)-2-bromo-paraxylene

The procedure used is that described in Example 1, except that instead of 72.6 parts only 69.5 parts of cyclopentadiene and instead of 149 parts of α,α',2,3,5,6-hexachloro-paraxylene 163 parts of α,α'-2-tribromo-paraxylene are used, to yield 98 parts of a dark brown, solid resin which has a softening point of 115° C.

Analysis: calculated Br 25.4% found 24.9%

Manufacturing the α,α',2-tribromo-paraxylene used in this example:

While heating 92.5 parts of bromo-paraxylene at a bath bath temperature of 130° C. and irradiating with ultraviolet light 160 parts of bromine are slowly dropped in. On cooling, a crystalline mass forms which is recrystallized from light petroleum (90 - 120° C.) to form colourless crystals of α,α',2-tribromo-paraxylene melting at 90 - 91° C.

EXAMPLE 5

Oligomeric α,α'-bis(cyclopentadienyl)-2,3,5-trichloro-paraxylene

The procedure used is as described in Example 1, except that 132.5 parts of α,α',2,3,5-pentachloro-paraxylene [m.p. 82–84° C.] instead of 149 parts of α,α',2,3,5,6-hexachloroparaxylene are used, to yield 110 parts of a light-yellow, solid resin having a softening point of 107° C. (Kofler heater).

| Analysis: | calculated | found |
|---|---|---|
| %C | 64.03 | 63.31 |
| % H | 4.48 | 4.60 |
| % Cl | 31.50 | 31.18 |
| Molecular weight: | 1140 | |

EXAMPLE 6

Oligomeric α,α'-bis(methylcyclopentadienyl)-2,3,5,6-tetrachloroparaxylene

The procedure used is as described in Example 1 except that instead of 72.6 parts of monomeric cyclopentadiene 88 parts of commercial monomeric methylcyclopentadiene are used (b.p. 70° C., a mixture consisting mainly of 2-methylcyclopentadiene and a small proportion of 1-methylcyclopentadiene) to yield 156 parts of a light-yellow, solid resin having a softening point of 76° C. (Kofler heater).

| Analysis: | calculated | found |
|---|---|---|
| % C | 60.03 | 59.81 |
| % H | 4.53 | 4.68 |
| % Cl | 35.44 | 35.22 |
| Molecular weight: | 980 | |

EXAMPLE 7

Oligomeric α,α'-bis(cyclopentadienyl)-2,5-difluoro-paraxylene

A suspension of sodium cyclopentadiene is prepared according to Example 1 from 23 g (1 mol) of sodium, 3 g of tertiary butyl alcohol and 72.6 g (1.1 mol) of monomeric cyclopentadiene. The suspension is washed on a glass fiber filter with 500 ml of toluene to free it from dimeric cyclopentadiene and tertiary butyl alcohol. The sodium cyclopentadiene is dissolved in the quantity of tetrahydrofuran required to give a 1-n solution.

In a 50 ml round flask, 0.615 g (2.91 mmols) of $\alpha,\alpha'$-dichloro-2,5-difluoro-para-xylene are treated under nitrogen at room temperature with 6.11 ml of a 1-n solution of sodium cyclopentadienate in tetrahydrofuran. The dichloride reacts at once and causes the temperature to rise by about 8° C. The dark violet solution is allowed to stand at room temperature for 1 hour. The solution is then slightly acidified with 0.3 ml of glacial acetic acid, the color changing to pale yellow. The batch is dissolved in 50 ml of benzene, the benzene solution agitated with 20 ml of water, the water is removed, and the benzene solution washed with 2 × 2 ml of saturated sodium chloride solution. The organic phase is dried with calcium chloride and concentrated under reduced pressure at 20° C. A pressure of 0.1 mm Hg and a temperature of 20° C. are maintained for 24 hours, and 0.638 g of a highly viscous brown resin obtained (81% of the theoretical yield).

Analysis: Oligomeric $\alpha,\alpha'$-bis(cyclopentadienyl)-2,5-difluoroparxylene.

Elementary analysis gives values close to the calculated values.

At 80° C. the resin gels within 30 minutes to form a rubber-like product. An infusible solid is obtained when the resin is cured at 200° C. for 1 hour with the exclusion of air.

The $\alpha,\alpha'$-dichloro-2,5-difluoro-paraxylene used in this Example is prepared as follows:

$\alpha,\alpha'$-dihydroxy-2,5-difluoro-paraxylene

A solution of 63.2 g (0.265 mols of 2,3,5,6-tetrafluoroterephthalic acid (m.p. 268 - 271° C., obtainable from Pierce-Chemical, Rockford, Ill., U.S.A., in 450 ml of tetrahydrofuran are introduced in the course of 1 hour into a solution of 40.3 g (1.06 mols) of lithium aluminium hydride in 1200 ml of tetrahydrofuran. The reaction mixture is refluxed for 24 hours, then cooled to 10° C. and treated carefully with 40 ml of 15% sodium hydroxide solution and finally with 120ml of water. The white precipitate is filtered off, washed with 500 ml of tetrahydrofuran, and the clear filtrate concentrated at 60° C. under vacuum. 37.9 g of slightly yellow-colored crystals are obtained. This-layer chromatography reveals them to be a mixture of at least three substances. To isolate a unitary substance, the batch is dissolved in 500 ml of ether, 2.8 g of insoluble constituents are removed by filtration, and the ethereal solution concentrated to one-third its volume. It is then treated with 35 ml of pentane and cooled to 10° C., white crystals precipitating. After two recrystallizations from ether+λ pentane, 3.4 g of fine needles are obtained which melt at 107–109° C.

| Analysis: $C_8H_8F_2O_2$ | calculated | found |
|---|---|---|
| % C | 55.17 | 55.38 |
| % H | 4.63 | 4.69 |
| % F | 21.82 | 21.5 |

The nuclear resonance spectrum of the above compound indicates that it has the structure of $\alpha,\alpha'$-dihydroxy-2,5-difluoro-para-ylene.

$\alpha,\alpha'$-dichloro-2,5-difluoro-para-xylene

While cooling with ice, 3 g of triethylamine are added to a mixture of 25 g of phosphorus pentachloride and 25 g of phosphorus oxychloride. After that, a solution of 2.2 g of $\alpha,\alpha'$-dihydroxy-2,5-difluoro-para-xylene in 10 ml of tetrachloromethane are added. The batch is heated at 70° C. for two hours. It is then cooled, poured onto ice, and dissolved in benzene. The benzene solution is washed with aqueous sodium carbonate solution, then dried with calcium chloride. The solvent is evaporated and the residue recrystallized several times from aqueous methanol. There are obtained 1.85 g of fine colorless needles melting at 62.5 - 64.5° C.

| Analysis: $C_8H_6Cl_2F_2$ | calculated | found |
|---|---|---|
| % C | 45.51 | 45.31 |
| % H | 2.87 | 3.13 |
| % F | 18.00 | 17.1 |

II. EXAMPLES OF USES

EXAMPLE A

About 12 g of the solid resin described in Example 1 are powdered and pregelled in a mould of polytetrafluoroethylene (TEFLON, registered trade mark) at 150° C. under a pressure of 50 kiloponds/cm² for 30 minutes. To finalize the curing the specimen is left in the press for another hour at 225° C. A light-yellow, clear, transparent panel is obtained.

The mould used was a TEFLON ® panel, 1.5 mm thick, with a window 70 × 100 mm cut out. The mould is closed with a TEFLON ® bottom plate and a TEFLON ® cover plate.

A test of the flammability according to ASTM-D-635 revealed a self-sustaining value of the flame of 0 seconds. The panel revealed the following dielectric test results:

Dependence of the loss factor tgδ and of the dielectric constant a on the frequency at 25° C.:

| Frequency (cycles) | tgδ × 10² (25° C) | ε (25° C) |
|---|---|---|
| 50 | 0.1 | 3.1 |
| 10³ | 0.27 | 2.7 |
| 10⁴ | 0.30 | 2.7 |
| 10⁵ | 0.30 | 2.7 |
| 10⁶ | 0.33 | 2.6 |
| 10⁷ | 0.43 | 2.5 |

EXAMPLE B

When instead of the solid resin of Example 1 the solid resin of Examples 2 is cured under the conditions described above, the following dielectric properties are found:

Dependence of the loss factor tgδ and of the dielectric constant ε on the frequency at 25° C.:

| Frequency (cycles) | tgδ × 10² (25° C) | ε (25° C) |
|---|---|---|
| 10³ | 0.14 | 2.7 |
| 10⁴ | 0.17 | 2.7 |
| 10⁵ | 0.15 | 2.7 |
| 10⁶ | 0.14 | 2.7 |
| 10⁷ | 0.20 | 2.7 |

EXAMPLES C AND D

When instead of the solid resin obtained in Example 1 the solid resin of Example 5 or, respectively, Example 6 is cured under the conditions described in Example A, the following dielectrical properties are found:
Dependence of the loss factor tgδ and of the dielectric constant $\epsilon$ on the frequency at 25° C.:

| Frequency cycles | Example C solid resin of Ex. 5 | | Example D solid resin of Ex. 6 | |
|---|---|---|---|---|
| | tgo × 10² | $\epsilon$ | tgo × 10² | $\epsilon$ |
| 50 | 0.20 | 2.8 | — | — |
| 10³ | 0.17 | 2.7 | 0.14 | 2.7 |
| 10⁴ | 0.11 | 2.7 | 0.11 | 2.7 |
| 10⁵ | 0.16 | 2.7 | 0.18 | 2.7 |
| 10⁶ | 0.20 | 2.7 | 0.21 | 2.7 |
| 10⁷ | 0.29 | 2.7 | 0.24 | 2.7 |

EXAMPLE E

A mixture of
600 g of a 67% solution of oligomeric $\alpha,\alpha'$-bis(cyclopentadienyl)-2,3,5,6-tetrachloro-paraxylene [prepared as described in Example 1] in toluene,
500 g of burnt kaolin (registered trademark MOLOCHIT),
100 g of barium sulphate
20 g of calcium stearate and
8 g of di-tertiary butylperoxybutane
was kneaded for 15 minutes in a divided-trough kneader to form a uniform dough which was then dried for 9 hours in a vacuum cabinet at 100° C. The solvent was then removed and the cooled, dry material disintegrated in a hammer mill. The resulting moulding composition was pressed at 190° C. and the mouldings revealed the following properties:
Heat distortion point according to Martens,

| DIN 53 458 | | | 117° C |
|---|---|---|---|
| flexural strength, VSM 77 103, | | | 5.3 kg/mm² |
| loss factor | | | |
| tgo × 10² at 20° C and | 50 | cycles/second | 4.32 |
| | 10³ | " | 4.08 |
| | 10⁴ | " | 3.37 |
| | 10⁵ | " | 3.36 |
| | 10⁶ | " | 2.67 |
| | 10⁷ | " | 1.96 |
| dielectric constant $\epsilon$ at 20° C and | 50 | " | 5.4 |
| | 10³ | " | 4.5 |
| | 10⁴ | " | 4.4 |
| | 10⁵ | " | 4.1 |
| | 10⁶ | " | 4.1 |
| | 10⁷ | " | 4.0 |
| flammability (ASTM-D-635) | | | 0 seconds |

EXAMPLE F

Manufacturing a glass laminate with oligomeric $\alpha,\alpha'$-bis(cyclopentadienyl)-2,3,5,6-tetrachloro-paraxylene A glass fibre fabric previously treated with a finish of vinyl-tris-(β-methoxy-ethoxy)-silane [registered trademark "A-172", makers Union Carbide] was impregnated by being dipped in a solution of 100 parts of oligomeric $\alpha,\alpha'$-bis(cyclopentadienyl)-2,3,5,6-tetrachloroparaxylene [manufactured as described in Example 1] and 0.5 part of di-tertiary butylperoxybutane in 100 parts of a mixture of equal parts of toluene and xylene. The fabric was then dried for 30 minutes at a temperature rising from 120 to 160° C. The resulting coated fabric had a resin content of 50%; it was bundled, covered on both sides with a TEFLON ® foil and inserted in a press heated at 200° C. The press plates were closed to mere contact pressure and after 3 minutes the pressure was increased to 20 kiloponds/cm². After pressing for 1 hour the whole was cooled to 50° C. and the resulting panel taken out of the press and its curing finalized for 6 hours at 200° C. in an oven. A firm, tough laminated panel was obtained which revealed the following properties:

| Resin content | | 46% |
|---|---|---|
| flexural strength (VSM 77 103) at 20° C | | 33 kp/mm² |
| | at 150° C | 33.2 kp/mm² |
| Water absorption (VSM test specimen) | | |
| | after 24 hours at 20 – 23° C | 0.10% |
| | after 1 hour at about 100° C | 0.10 – 0.20% |
| flammability (ASTM-D-635) | | 0 seconds |
| specific resistance (DIN 53 482) | | 10¹⁶ Ohm × cm |
| dielectric loss factor tgo × 10², 50 c/s, | | |
| 1000 Volts at 20° C | | 0.4 |
| 100° C | | 0.4 |
| 150° C | | 0.4 |
| 200° C | | 0.5 |
| 240° C | | 4.1 |
| dielectric constant $\epsilon$ at 1Mc/sec., at 25° C | | 3.7 |

In the identical manner a laminate was manufactured which had its adhesion improved by facing it unilaterally with a roughened copper foil. This foil adhered firmly to the surface of the laminate.

EXAMPLE G

Manufacturing a flameproof glass laminate with a mixture of oligomeric $\alpha,\alpha'$-bis(cyclopentadienyl)-2,3,5,6-tetrachloro-paraxylene and oligomeric 1,6-bis(cyclopentadienyl)hexane 100 Parts of oligomeric $\alpha,\alpha'$-bis(cyclopentadienyl)-2,3,5,6-tetrachloro-paraxylene and 20 parts of the oligomeric 1,6-bis(cyclopentadienyl)hexane described below are dissolved in a solvent mixture of 33 parts of toluene, 33 parts of xylene and 10 parts of a mixture of aromatic hydrocarbons, marketed under the trademark SOLVESSO 100. A glass fibre fabric having a finish of vinyl-tris(methoxy-ethoxy)silane [registered trademark "A-172," makers Union Carbide] is impregnated by being dipped in this solution and then dried for 23 minutes at a temperature rising from 100 to 140° C. The resulting coated fabric has a resin content of 48%; it is bundled, covered on both sides with TEFLON ® foils and inserted in a press heated at 180° C. The press plates are closed to mere contact pressure and after 5 minutes the pressure is increased to 20 kg/cm². Within 10 minutes the temperature is then raised to 200° C. and pressing is performed at this temperature for 2 hours. After this time the whole is carefully cooled for 30 minutes to 50° C. and the panel thus formed is taken out of the press. It is a tough laminate having a resin content of 40%; it is flameproof and has good electrical properties;
Flammability according to ASTM-D-635: 0 seconds
dielectric constant $\epsilon$ at 1Mc/s (25° C.): 3.8

The oligomeric 1,6-bis(cyclopentadienyl)hexane was prepared in the following manner:

A dispersion of 138 g of sodium in 800 g of xylene was mixed with 18 g of tertiary butanol and 436.2 g of monomeric cyclopentadiene were stirred in dropwise at 45° C. The mixture was heated for 2 hours at 45° C., then raised to the boil and 441.6 g of 1,6-dichlorohexane were dropped in. On completion of the dropwise addition 3.0 g of poly(2,2,4-trimethyl-1,2-dihydroquinoline) were added and the whole was heated for another 4 hours at the boil, then cooled, neutralized with a small quantity of glacial acetic acid, the precipitated sodium chloride was filtered off and thoroughly rinsed with xylene. After having distilled off the xylene under a vacuum of 15 mm Hg up to 130° C., there were obtained 552 g of the light-brown oligomeric 1,6-bis(cyclopentadienyl)hexane having a viscosity of 100,000 centipoises at 25° C. and a colour number (according to Gardner and Holdt) of 15. The molecular weight of the oligomer was 1125, corresponding to a polymerization degree of 5.

What is claimed is:

1. An oligomer of monomeric halogenated bis(cyclopentadienyl) compound having the formula

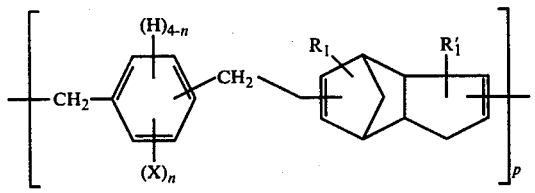

in which p is 2 to 4, X is fluorine, bromine or chlorine, $R_1$ and $R_1'$ each is hydrogen or methyl and n is an integer of at least 1 and at most 4.

2. An oligomer of claim 1 of $\alpha,\alpha'$-Bis(cyclopentadienyl)-2,3,5,6-tetrachloro-para-xylene.

3. An oligomer of claim 1 of $\alpha,\alpha'$-Bis(cyclopentadienyl)-2,3,5-trichloro-para-xylene.

4. An oligomer of claim 1 of $\alpha,\alpha'$-Bis(methylcyclopentadienyl)-2,3,5,6-tetrachloro-para-xylene.

5. An oligomer of claim 1 of $\alpha,\alpha'$-Bis(cyclopentadienyl)-2,5-difluoro-para-xylene.

6. The cured product obtained by heating the oligomer of claim 1 within the range of from about 135° to 280° C., optionally in the presence of a curing catalyst.

7. A method for preparing the oligomer of claim 1 which comprises reacting a compound of the formula

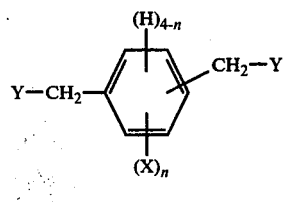

wherein
Y is chloro or bromo,
X is fluoro, bromo or chloro,
n is 1 to 4, with cyclopentadiene or methylclopentadiene, in the presence of an alkali metal or a Grignard compound.

* * * * *